(12) United States Patent
Liu et al.

(10) Patent No.: US 9,789,232 B2
(45) Date of Patent: Oct. 17, 2017

(54) MEDICAL INSTRUMENT COATING AND PREPARATION METHOD THEREFOR AND MEDICAL INSTRUMENT COMPRISING COATING

(71) Applicant: Lifetech Scientific (Shenzhen) Co., Ltd., Shenzhen (CN)

(72) Inventors: Hengquan Liu, Shenzhen (CN); Lihua Dong, Shenzhen (CN)

(73) Assignee: Lifetech Scientific (Shenzhen) Co. Ltd. (CN)

( * ) Notice: Subject to any disclaimer, the term of this patent is extended or adjusted under 35 U.S.C. 154(b) by 272 days.

(21) Appl. No.: 14/652,419

(22) PCT Filed: Dec. 4, 2013

(86) PCT No.: PCT/CN2013/088559
§ 371 (c)(1),
(2) Date: Jun. 15, 2015

(87) PCT Pub. No.: WO2014/094543
PCT Pub. Date: Jun. 26, 2014

(65) Prior Publication Data
US 2015/0320912 A1    Nov. 12, 2015

(30) Foreign Application Priority Data
Dec. 21, 2012 (CN) .......................... 2012 1 0562809

(51) Int. Cl.
*C23C 14/16* (2006.01)
*A61L 31/08* (2006.01)
(Continued)

(52) U.S. Cl.
CPC .......... *A61L 31/088* (2013.01); *A61L 31/022* (2013.01); *C23C 14/165* (2013.01); *C23C 14/34* (2013.01);
(Continued)

(58) Field of Classification Search
CPC ......... C23C 14/06; C23C 14/14; C23C 14/16; C23C 14/165; C23C 16/408; A61L 31/022
See application file for complete search history.

(56) References Cited

U.S. PATENT DOCUMENTS

2004/0191556 A1* 9/2004 Jardine .................. C22C 30/00
428/610
2010/0143741 A1* 6/2010 Bell ........................ C23C 18/54
428/551

FOREIGN PATENT DOCUMENTS

WO    WO 9639547 A2 * 12/1996 .............. C22F 1/006

OTHER PUBLICATIONS

Yoshimoto, Ken-ichi. "Cu—Ti intermetallic compound film deposited by co-sputtering" Asahikawa Kogyo Koto Senmon Gakko Kenkyu Hobun vol. 32 pp. 29-35. 1995. Translation.*
(Continued)

*Primary Examiner* — Mike M Dollinger
*Assistant Examiner* — Christina Wales
(74) *Attorney, Agent, or Firm* — Raymond Sun

(57) ABSTRACT

Disclosed is a medical instrument coating, being coated on the surface of a nickel-titanium alloy component of a medical instrument. The medical instrument coating comprises an elementary copper phase, an amorphous titanium-containing substance and a transition layer comprising a copper-nickel intermetallic phase. Also mentioned is a preparation method for the medical instrument coating. A medical instrument comprising a copper-titanium coating has good blood compatibility, and simultaneously can inhibit the endothelialization of the medical instrument surface, thereby improving the recovery rate of the medical instrument and prolonging the recovery time window; the copper-titanium coating belongs to the group of metal composite coatings, has a certain toughness and ductility, and
(Continued)

avoids the large-amplitude deformation process of the medical instrument damaging the coating; and the mechanical property and the coating quality of the medical instrument comprising a fine nickel-titanium alloy component are guaranteed by the method for preparing the coating.

5 Claims, 4 Drawing Sheets

(51) Int. Cl.
    *C23C 14/34*      (2006.01)
    *A61L 31/02*      (2006.01)

(52) U.S. Cl.
    CPC ....... *C23C 14/3485* (2013.01); *A61L 2420/02* (2013.01); *A61L 2420/06* (2013.01); *Y10T 428/265* (2015.01)

(56) References Cited

OTHER PUBLICATIONS

Liu, H. et al "Hemocompatibility and anti-endothelialization of copper-titanium coating for vena cava filters" Surface & Coatings Technology 206 (2012) 3501-3507.*

XPS Interpretation of Copper. Available at: http://xpssimplified.com/elements/copper.php 1/ accessed Jun. 15, 2017.*

Elzey, S. et al "Formation of paratacamite nanomaterials via the conversion of aged and oxidized copper nanoparticles in hydrochloric acidic media" Journal of Materials Chemistry 2011, 21, 3162.*

\* cited by examiner

MEDICAL INSTRUMENT COATING AND PREPARATION METHOD THEREFOR AND MEDICAL INSTRUMENT COMPRISING COATING

TECHNICAL FIELD

The present invention relates to a medical instrument, and relates to a medical instrument coating for inhibiting cell growth and a preparation method thereof, and a medical instrument particularly suitable for a short-term implantation having a fine nickel-titanium alloy component.

BACKGROUND OF THE INVENTION

Morbidity and diagnostic yield of Deep Venous Thrombosis (DVT) and Pulmonary Thromboembolism (PE) increase day by day. The PE, as the most serious complication of the DVT, has a higher morbidity and case fatality rate. It was reported in literature that the yearly morbidity of DVT in the total population in western countries was between 0.05% and 0.1%, and there were about 30 million patients having DVT and sequelae in China. Due to a potential risk of a fateful Pulmonary Embolism (PE) caused by caduceus blood clots, it has become a difficult problem of a clinical treatment. An application of an Inferior Vena Cava Filter (IVCF) not only may effectively avoid pulmonary embolism, but also makes thrombolysis and surgical treatment safer. It was shown by an analysis that a placement of the IVCF could effectively prevent PE, and decreased the PE incidence rate of DVT patients from 60%-70% down to 0.9%-6%, and the incidence rate of fateful PE down to 0.7%-4%. Due to effective PE prevention, a small operative wound, simple operation and few complications, the IVCF has been regarded as a preferred method for preventing PE.

The Inferior Vena Cava Filter (IVCF), an instrument formed by weaving metal wires or carving a whole metal block by lasers, is placed in the inferior vena cava by a special conveying device to form a reticular protection structure for obstructing large blood clots. A common inferior vena cava filter includes fine support rods generally made from super-elastic nickel-titanium alloys. The present IVCFs may be classified into recoverable and permanent implantation filters, where the permanent implantation filters may result in lifelong use of anticoagulants or other complications because they are placed in the human body for a long period of time. It can be seen from clinical application data of IVCFs implanted into the human body for 5 years that the ratio of the permanent filters is gradually reduced and the recoverable filters have been preferred by patients. The present recoverable filters are mainly realized in structural design. For example, in Chinese Patent No. CN2569770Y, Y-shaped rods are designed on a conical surface net end, which was convenient for filter recovery; Chinese Patent Publication No. CN1868549A employs an opening design, where a spiral funnel shape was formed by metal wires and a plurality of metal wires were radially woven; other Chinese Patents (Issued Nos. CN2710575Y, CN200942133Y, CN201088640Y, among others). also realize the recovery of filters in structural design. All the above filters use structure to change the recovery time as a technical solution. Although the recovery rate and recovery time window of filters may be improved to a certain extent, the embedding of cells on the surfaces of the filters and degree of endothelialization cannot be basically inhibited. Meanwhile, as the majority is based on unsymmetrical single umbrellas in this design, such a structure has a poor geometric stability, and the filters are likely to generate displacement and inclination. Furthermore, the poor geometric stability also results in the rod crack of filters and the damage to vessel walls during recovery.

Seen from main manufacturers of recoverable filters in the world, the patents of Cook Inc., C.R. BARD, ALN and other companies realize the recovery of filters through an umbrella-shaped structure, but they all share the same problem in their clinical applications: the recovery time window of a present short-term implantable medical instrument, particularly of recoverable vena cava filters, is very short; moreover, as the recoverable vena cava filters are in contact with the inner wall of blood vessels, the recovery time of the filters is short or the filters cannot recovered be successfully due to the embedding of endothelial cells, the migration of smooth muscle and the encapsulation of tissue-like substances, so that the vessel walls may be damaged if the filters are forcibly recovered.

Some researchers tried to prepare a drug coating on the surface of a filter. For example, in Chinese Patent Publication Nos. CN101843531A and CN201870771, a polymer coating is coated on the surface of a filter by antithrombotic and thrombolytic drugs or other drugs, so that the antithrombus and the inhibition to cell embedding are realized by slowly releasing the drugs. Chinese Patent Publication No. CN102330059A employs plasma polymerization to prepare a hydrophobic material (like polyethylene glycol, PEG-L) on the surface of the filter so as to inhibit the embedding of protein and cells. The high-molecular polymer is prepared on a metal substrate in this technical solution, but the polymer coating is likely to crack and fall off during a deployment process of the filter because the metal and polymer have large differences in stiffness, toughness and other physical properties, thereby resulting in insufficient drug administration or new thrombosis sources, and influencing the effectiveness of the filter.

In particular cases, other medical instruments (e.g., intravascular stents) implanted in the human body are also required to be recovered, and the growth of cells on the surfaces of the medical instruments is also required to be inhibited within a certain time. Similar to the vena cava filters, those medical instruments are often fine components made from nickel-titanium alloys, and a coating is required to be manufactured on the fine components. The medical instruments, which are implanted in the human body in an interventional manner, are commonly made from super-elastic nickel-titanium alloys, but the polymer coating is likely to crack and fall off during the deformation and deployment process of the medical instruments, thereby resulting in insufficient drug administration or new thrombosis sources. However, the coating having metallic characteristics may realize better adhesion and ductility on the nickel-titanium alloy surface. Considering that the medical instrument coating in the prior art cannot give consideration to both the better mechanical property and the effective inhibition of cell growth, the present invention employs plasma sputtering deposition to prepare a copper-titanium coating on a surface of a medical instrument. The copper-titanium coating has a good bonding force with a nickel-titanium alloy substrate, a high ductility, the stiffness, toughness and other physical properties, which can meet the mechanical requirements for a large-amplitude deformation of the medical instrument; and the copper-titanium coating continuously releases copper ions in the human body, and thus may effectively inhibit the embedding of cells on the surface of the medical instrument, thereby prolonging the recovery time window of the medical instrument.

At present, the technical problem that a copper-titanium coating capable of releasing copper ions is prepared on the surface of a medical instrument having a fine nickel-titanium alloy component is not well solved. Depositing a coating on a medical instrument having a fine nickel-titanium alloy component by a plasma technology needs to solve the following technical difficulties:

during the preparation process of the coating, plasma is moved to a substrate at a high speed under the action of a sputtering bias voltage, and irons "bombard" the surface of the substrate to generate lots of heat to quickly heat the fine nickel-titanium alloy component, so that the Austenite final temperature $A_f$ of the nickel-titanium alloy is increased, but the mechanical properties of the medical instrument are reduced;

during preparing a coating on the surface of the fine nickel-titanium alloy component by a plasma deposition method, as the effective contact area of the plasma with the nickel-titanium alloy surface is small, there is not enough time for ions carrying with energy to quickly spread on the surface, so that a part of ions are "accumulated" or the stress of the coating is concentrated, and the bonding force of the coating thus cannot meet application requirements; and as the copper-titanium coating releasing copper ions is degradable, the microstructure, bonding force and compactness of the coating directly influence the degradation characteristics of the copper-titanium coating, but the present technological characteristics cannot guarantee the requirements for the ion release rate of the coating; and, as the ratio of two elements in content influences the functionality of the copper-titanium coating, it is required to optimize quality percentages of elements in the coating on the basis of the improvements of deposition methods in the prior art.

SUMMARY OF THE INVENTION

Technical Problem

A technical problem to be solved by the present invention is to provide a medical instrument coating, the toughness and ductility of which may adapt to the large-amplitude elastic deformation of the medical instrument; meanwhile, within a long enough time, the coating may stop the growth of cells on the surface of the medical instrument, inhibit endothelialization of the medical instrument surface, and prolong the recovery time window, thereby improving the recovery rate of the medical instrument implanted in the human body.

Technical Solutions

To solve the technical problem of the present invention, a technical solution is employed: a medical instrument coating is provided, being coated on the surface of a nickel-titanium alloy component of a medical instrument, wherein the medical instrument coating contains an elementary copper phase, an amorphous titanium-containing substance and a transition layer including a copper-nickel intermetallic phase.

As a further improvement of the medial instrument coating provided by the present invention, a medical instrument includes at least one fine nickel-titanium alloy component, with a area of at least one cross-section of the fine nickel-titanium alloy component being not more than 3 mm².

As a further improvement of the medical instrument coating provided by the present invention, the area of at least one cross-section of the fine nickel-titanium alloy component is not more than 1 mm².

As a further improvement of the medial instrument coating provided by the present invention, the medical instrument coating basically has no copper-titanium intermediate phase, and a majority of copper atoms are in an elementary state.

As a further improvement of the medial instrument coating provided by the present invention, the copper content of the medical instrument coating is in a range from 40% to 80%.

As a further improvement of the medial instrument coating provided by the present invention, a thickness of the medical instrument coating is in a range from 200 nm to 300 nm.

As a further improvement of the medial instrument coating provided by the present invention, in human body, a majority of copper elements of the medical instrument coating can be released in form of copper ions.

As a further improvement of the medial instrument coating provided by the present invention, in human body, the time required for releasing all the copper elements of the medical instrument coating is in a range from 50 days to 60 days.

Another technical problem to be solved by the present invention is to provide a method for preparing a copper-titanium metal coating on a surface of a medical instrument having a nickel-titanium alloy component. The method makes the coating have better biological properties, and the mechanical properties of both the medical instrument and the coating are ensured by the method.

To solve another technical problem of the present invention, the following technical solution is employed: a method for preparing a coating on a surface of a nickel-titanium alloy component of a medical instrument is provided, and the method includes the following steps:

step 1: cleaning and drying a surface of a nickel-titanium alloy component of a medical instrument;

step 2: generating copper ions and titanium ions in a vacuum chamber, and forcing the copper ions and the titanium ions to move to the surface of the nickel-titanium alloy component of the medical instrument under the action of a bias voltage; and step 3: keeping a temperature of the surface of the nickel-titanium alloy component to be between 50° C. and 200° C., and allowing the copper ions and the titanium ions to form a copper-titanium coating on the surface of the nickel-titanium alloy component.

In the preparation method of a coating provided by the present invention, in step 2, both the copper ions and the titanium ions are generated by a pulse sputtering method.

In the preparation method of a coating provided by the present invention, a pulse width employed by the pulse sputtering method is in a range from 15 ms to 30 ms.

In the preparation method of a coating provided by the present invention, in step 2, the bias voltage is in a range from 50 V to 100 V.

In the preparation method of a coating provided by the present invention, in step 2, the pressure in the vacuum chamber is in a range from 0.2 Pa to 0.8 Pa. The pressure in the vacuum chamber is in a range from 0.3 Pa to 0.5 Pa.

In the preparation method of a coating provided by the present invention, in step 3, a temperature of the surface of the nickel-titanium alloy is kept to be between 100° C. and 150° C.

The present invention further provides a medical instrument coating prepared by the above-mentioned method.

The present invention further provides a medical instrument containing the above-mentioned coating.

Beneficial Effects

Compared with the prior art, the present invention has the following advantages: (1) the medical instrument containing the copper-titanium coating provided by the present invention has good blood compatibility, and simultaneously can inhibit the endothelialization of the medical instrument surface, thereby improving the recovery rate of the medical instrument and prolonging the recovery time window; (2) the copper-titanium coating belongs to the group of metal composite coatings, has a certain toughness and ductility, and avoids the large-scale deformation process of the medical instrument damaging the coating; and (3) the mechanical property and the coating quality of the medical instrument having a fine nickel-titanium alloy component are guaranteed by the method for preparing the coating.

BRIEF DESCRIPTION OF THE DRAWINGS

The present invention will be further described as below with reference to accompanying drawings and embodiments, wherein.

DETAILED DESCRIPTION OF THE INVENTION

Figure 1:
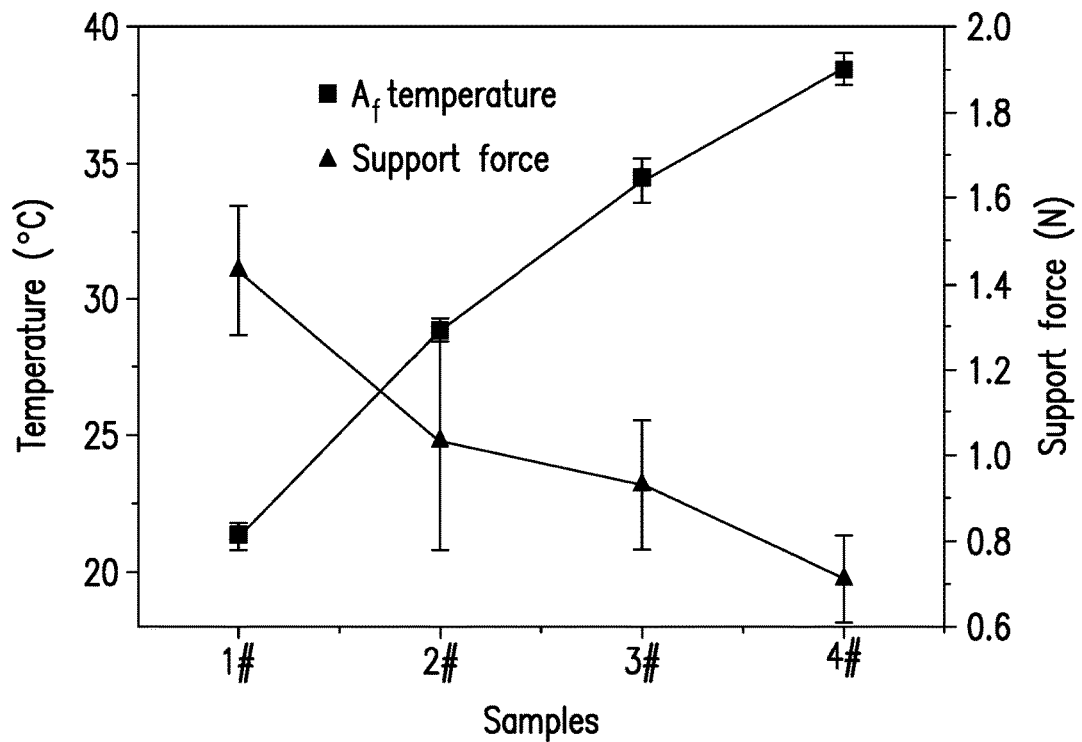
FIG. 1 shows change curves of $A_f$ temperature and radial support force of a filter deposited with a copper-titanium coating at different temperatures and at a bias voltage of 100 V.

To make the objectives, technical solutions and advantages of the present invention clearer, the present invention will be further described as below in details with reference to the accompanying drawings and embodiments. It should be understood that the specific embodiment described herein are merely for explaining the present invention, and not intended to limit the present invention.

The present invention provides a copper-titanium metal coating prepared on the surface of a medical instrument having a fine nickel-titanium alloy component. Within a long enough time (e.g., 60 days), the coating may stop the growth of cells on the surface of the medical instrument, inhibit endothelialization of the medical instrument surface, and prolong the recovery time window, thereby improving the recovery rate of the medical instrument implanted in human body. The present invention further provides a method for preparing the coating. The method makes the coating have better biological properties, and the mechanical properties of both the medical instrument and the coating are ensured by the method. The toughness and ductility of the coating may adapt to the large-scale elastic deformation of the medical instrument. To achieve optimizations, it is necessary to select proper coating deposition conditions to optimize the microstructure and compositions of the coating.

The present invention has the following advantages: (1) the medical instrument containing the copper-titanium coating provided by the present invention has good blood compatibility, and simultaneously can inhibit the endothelialization of the medical instrument surface, thereby improving the recovery rate of the medical instrument and prolonging the recovery time window; (2) the copper-titanium coating belongs to the group of metal composite coatings, has a certain toughness and ductility, and avoids the large-amplitude deformation process of the medical instrument damaging the coating; and (3) the mechanical property and the coating quality of the medical instrument having a fine nickel-titanium alloy component are guaranteed by means of the method for preparing the coating.

The specific structure, preparation method and other aspects of the medical instrument coating provided by the present invention will be illustrated by multiple embodiments. Hereinafter, the medical instruments are respectively described by taking a vena cava filter and an intravascular stent for an example.

Embodiment 1

A copper-titanium coating is prepared on a surface of a vena cava filter made of nickel-titanium memory alloy. The structure of the vena cava filter has been described in details in the prior art. A main portion of the vena cava filter includes a filter screen composed of a plurality of fine support rods, with a cross-sectional area of each of the support rods being not more than 1 $mm^2$. The vena cava filter having a fine nickel-titanium alloy structure is first cleaned, dried and stored in a dry vessel for standby. The target material of the cathode is titanium target (Ti 99.99%) and copper target (Cu 99.99%). In a vacuum chamber, the target material is heated by a certain target current such that titanium atoms and copper atoms are evaporated and ionized on the surface of the target material. Under the action of a sputtering bias voltage, titanium ions and copper ions in a certain proportion are moved to the surface of the vena cava filer so as to form a copper-titanium coating on the surface of the vena cava filter.

During the preparation process of the copper-titanium coating, plasma is moved to a nickel-titanium alloy substrate at a high speed under the action of a bias voltage, and irons "bombard" the surface of the substrate to generate lots of heat to quickly heat the fine nickel-titanium alloy component. Under a higher sputtering bias voltage, even though the heating power supply is turned off, the fine nickel-titanium alloy component is still kept at a certain temperature, generally above 50° C. As the phase inversion temperature $A_f$ of the nickel-titanium memory alloy is sensitive to the heat treatment temperature and time, an over-high temperature will increase the phase inversion temperature $A_f$ of the nickel-titanium memory alloy, and reduce the mechanical properties of a medical instrument.

Taking a vena cava filter as an example, to ensure the mechanical property of the fine support rods of the vena cava filter and the quality of the copper-titanium coating, the copper-titanium coating is realized by the following steps.

First, the surface of the vena cava filter is cleaned by ion sputtering. The vena cava filter is placed in a vacuum chamber, then argon is fed for sputtering cleaning the vena cava filter for 3-5 min when the pressure of the vacuum chamber is reduced to $3.0 \times 10^{-3}$ Pa.

Then, the pressure of the vacuum chamber is reduced to $5.0 \times 10^{-5}$ Pa, and a heating power supply is enabled to increase the temperature of the filter up to 150° C. Argon is fed to keep the pressure of the vacuum chamber at 0.5 Pa, and copper target and titanium target power supplies are enabled, respectively, where the current of the copper target is 60 A, the current of the titanium target is 50 A, the DC bias voltage of the pulse sputtering is adjusted to 100 V, the pulse width is about 20 ms, the pulse duty ratio is 90%, and the deposition time is 15 minutes. Generally, the pressure needs to be kept at 0.2-0.8 Pa, and it is possible that the pulse width is between 15 ms and 30 ms.

Finally, the bias voltage power supply and the target current are disabled, and the vena cava filter including a copper-titanium coating is taken out of the vacuum chamber after the vena cava filter in the vacuum chamber is cooled below 100° C.

By the above steps, the copper-titanium coating having a thickness of about 300 nm may be obtained. Through a XPS test, the copper content of the coating is about 55%, and the titanium content is about 45%.

Embodiment 2

Under the same pressure of the vacuum chamber, the same target current, the same sputtering bias voltage and the same pulse duty ratio, the mechanical property of the vena cava filter is controlled by changing the temperature of the vena cava filter (i.e., the deposition temperature of the coating).

For example, the heating power supply is enabled and kept at a high power to increase the temperature of the vena cava filter up to 200° C., the sputtering bias voltage is adjusted to 50V, and other conditions refer to Embodiment 1, so that a copper-titanium coating having a thickness of about 200 nm may be obtained. Through a test, the copper content of the coating is as much as that of the copper-titanium coating in Embodiment 1 because the copper target current and the titanium target current, as primary factors for determining the copper content of the copper-titanium coating, remains unchanged.

The heating power supply is kept at a lower power to increase the temperature of the vena cava filter up to 100° C., the bias voltage is adjusted to 100V, and other conditions refer to Embodiment 1, so that a copper-titanium coating having a thickness of about 200 nm may be obtained. The copper content of the coating is as much as that of the copper-titanium coating in Embodiment 1.

The phase inversion temperature is an important factor influencing the mechanical property of the nickel-titanium alloy, but the Austenite final temperature $A_f$ is an important index reflecting the "memory effect" and "super-elasticity" of the nickel-titanium alloy. As shown in FIG. 1, FIG. 1 shows changes in the radial support force and $A_f$ temperature of vena cava filters after copper-titanium coatings are deposited at different temperatures. Four samples in FIG. 1 are identical filters having fine components (support rods), and the copper-titanium coatings are prepared with reference to the above embodiments, where the sputtering bias voltage is 100V, and the copper content of each of the copper-titanium coating is about 55%. The filters formed with copper-titanium coatings at different temperatures are marked with different numbers, where #1 is a filter obtained after preparing a copper-titanium coating on a vena cava filer at a temperature of 50° C., #2 is a filter formed with a copper-titanium coating at 100° C., #3 is a filter formed with a copper-titanium coating at 150° C., and #4 is a filter formed with a copper-titanium coating at 200° C. It can be seen from FIG. 1 that, with the increase of the deposition temperature of the coating, the $A_f$ temperature of the nickel-titanium alloy in the filter increases, the super-elasticity of the nickel-titanium alloy component becomes poorer. and the radial support force of the vena cava filter is reduced. As the copper-titanium coating of the #1 filter sample is prepared at a low temperature (50° C.), the $A_f$ temperature is 17.5° C., and the vena cava filter has better super-elasticity and overall, mechanical property; but, the copper-titanium coating deposited at a low temperature has poor compactness, and the bonding force of the copper-titanium coating with the nickel-titanium alloy substrate is not good enough. This is mainly because the temperature influences the heat diffusion speed of ions on the surface of the filter. A low temperature will makes ions insufficiently diffuse after reaching the surface of the filter, thereby resulting in "accumulation" of irons or concentrated stress, and reducing the bonding force between the coating and the substrate. However, for the #2 sample, the copper-titanium coating deposited at 100° C. does not have such a defect. For #3 sample, the coating has good compactness and mechanical property, but the mechanical property and super-elasticity of the vena cava filter are reduced due to high deposition temperature (150° C.) of the coating; and, the $A_f$ temperature of the nickel-titanium alloy is 34.4° C., and the radial support force of the vena cava filer basically meet the requirements. However, as the deposition temperature of the coating of the #4 sample is up to 200° C., the radial support force of this filter sample has been obviously deteriorated. If the deposition temperature of the copper-titanium coating exceeds 200° C., it is harder to make the vena cava filter meet the design requirements. An important reason is that very fine support rods of the filter have obvious influences on the deposition process of the copper-titanium coating.

Comprehensively considering the mechanical property requirement of the nickel-titanium alloy medical instrument and the quality of the copper-titanium coating, in the preparation process of a medical instrument including a copper-titanium coating, the deposition temperature of the copper-titanium coating preferably ranges from 100° C. to 200° C., which is particularly suitable for the copper-titanium coating of a fine nickel-titanium alloy component.

Adjusting the pulse duty ratio of the sputtering bias voltage may change a deposition rate of copper-titanium coatings so as to obtain copper-titanium coatings having different thicknesses within the same time. For example, if the pulse duty ratio of the sputtering bias voltage is 20%, the deposition time is 15 minutes, and other conditions are the same as Embodiment 1, a copper-titanium coating having a thickness of about 50 nm may be obtained; and, if the pulse duty ratio is 60%, the deposition time is 15 minutes, and other conditions are the same as Embodiment 1, a copper-titanium coating having a thickness of about 200 nm may be obtained.

Through the in-vivo implantation and in-vitro simulation experimental researches of a recoverable filter, in combination with the bonding force of a copper-titanium coating and the degradation speed of the copper-titanium coating in vivo, the thickness of the copper-titanium coating on the surface of a filter is preferably in a range from 200 nm-300 nm. To improve the deposition efficiency of the coating, and reduce the influence of the sputtering heating effect on the deposition temperature of the coating and the mechanical property of the filter, the deposition time preferably ranges from 10 minutes to 30 minutes.

Adjusting the copper target current and the titanium current according to the ionization characteristics of the copper target and the titanium target may change the compositions of the copper-titanium coating. If the copper target current is controlled to be 60 A, the titanium current is 10 A, and other conditions refer to Embodiment 1, the copper mass percentage of the obtained copper-titanium coating is about 75% while the titanium mass percentage thereof is about 25%.

If the copper target current is controlled to be 30 A, the titanium current is 60 A, and other conditions refer to Embodiment 1, the copper mass percentage of the obtained copper-titanium coating is about 15% while the titanium mass percentage thereof is about 85%.

The copper/titanium mass ratio of the copper-titanium coating directly influences the biological property of a vena cava filter, the content of copper element in the copper-titanium coating influences the ability to inhibit the climbing of cells, while titanium element may dilute the "concentration" of copper atoms in the copper-titanium coating, and improve the blood compatibility of the copper-titanium coating. For example, a copper-titanium coating having a copper mass percentage more than 10% can inhibit the growth of cells thereon. For example, when the titanium mass percentage is higher, the copper-titanium coating has a better blood compatibility. Therefore, the coating having a different copper/titanium mass ratio is selected according to the actual environmental requirements of a recoverable vena cava filter in vivo.

Figure 2:
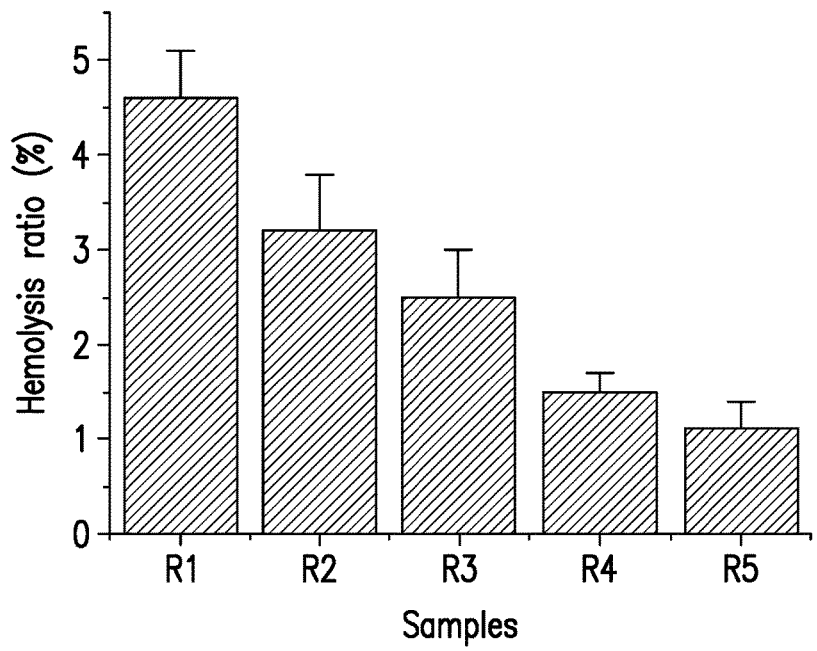
FIG. 2 is a comparison diagram of hemehysis ratios of copper-titanium coatings having different copper contents.

FIG. 2 shows hemolysis ratios of copper-titanium coatings having different compositions on the surface of a filter. The samples in FIG. 2 are marked with different numbers, where R1 is a copper-titanium coating containing 80% of copper (mass percentage), R2 is a copper-titanium coating containing 60% of copper, R3 is a copper-titanium coating containing 40% of copper, R4 is a copper-titanium coating containing 20% of copper, and R5 is a copper-titanium coating containing 10% of copper. It can be seen that, with the increase of the copper content in the copper-titanium coating, the hemolysis ratio is increasing. The hemolysis ratio of the copper-titanium coating having a copper mass percentage of 80% is very close to 5%, while the material having a hemolysis more than 5% does not conform to the requirement of bio-medical safety. Therefore, if a copper-titanium coating is deposited on a fine nickel-titanium alloy component, the copper content (i.e. copper mass percentage) is preferably lower than 80%.

The compositions and microstructure of a copper-titanium coating may be controlled by deposition parameters of the coating. The microstructure of the copper-titanium coating will influence the release process of copper ions. Actually, by controlling the number of target-ionized atoms through the target current, the control of the target current may directly influence the portion of each element in the coating, and thus influences the physical and chemical properties of the coating. As the copper target current and the titanium target current are primary factors controlling the atom number ratio of the copper-titanium coating, copper-titanium coatings having very different copper contents may be obtained by adjusting the copper target current and the titanium target current within a large range. As described in the embodiments, when the copper target current is 60 A and the titanium target current is 10 A, the copper mass percentage of the obtained copper-titanium coating is about 75% while the titanium mass percentage thereof is about 25%; when the copper target current and the titanium target current are 60 A and 50 A, respectively, the copper mass percentage and titanium mass percentage of the coating are 55% and 45%, respectively; and, when the copper target current and the titanium target current are 30 A and 60 A, respectively, the copper mass percentage and titanium mass percentage of the coating are 15% and 85%, respectively. The pressure influences the density of charged particles ionized by gas in the vacuum chamber. The number of ions reaching a unit area of the instrument surface under the action of a bias voltage is decreased as the pressure is reduced. A lower pressure may inhibit the formation of copper-titanium intermetallic compound so that the coating structure is optimized. To obtain a better copper-titanium coating, the pressure of the vacuum chamber is in a range from 0.2 Pa to 0.8 Pa. The sputtering bias voltage influences the rate of movement of the charged particles toward the instrument surface, and thus determines the energy of different particles reaching the instrument surface. A lower bias voltage will also inhibit the formation of copper-titanium intermetallic compound, and thus influences the coating structure. For example, the bias voltage ranging from 50V to 100V facilitates the formation of a copper-titanium coating having less copper-titanium intermetallic compound, and can improve the bonding force of the copper-titanium coating and a nickel-titanium alloy substrate. Therefore, by properly controlling the target current, sputtering bias voltage, gas flow and other deposition parameters, the compositions and microstructure of the coating are optimized.

Figure 3A:
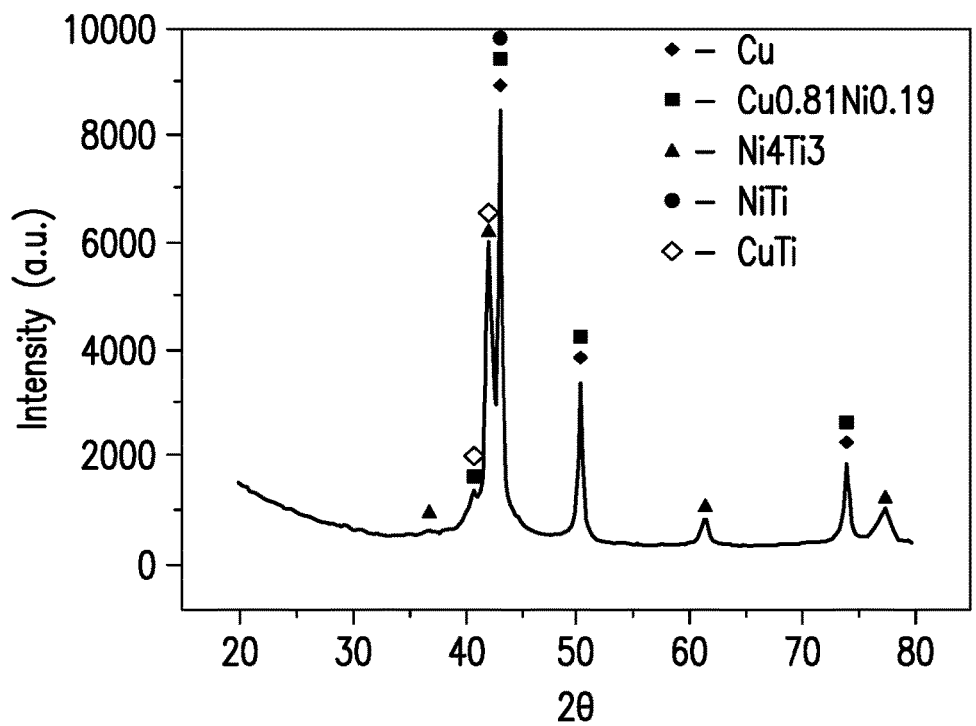
FIG. 3A is an XRD diagram of a copper-titanium coating, where the sputtering bias voltage is 100 V and the pressure is 0.5 Pa.
Figure 3B:
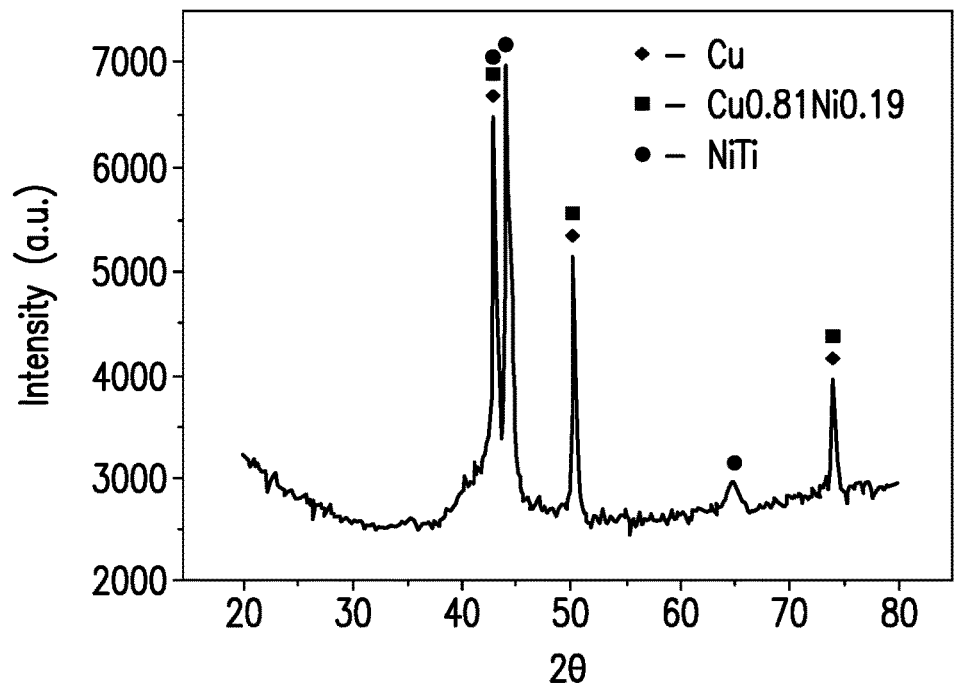
FIG. 3B is an XRD diagram of another copper-titanium coating, where the sputtering bias voltage is 50 V, the pressure is 0.3 Pa and other conditions are the same as that in FIG. 3A.

FIG. 3A shows an XRD graph of a copper-titanium coating deposited on the surface of a filter, where the copper target current is 60 A, the titanium target current is 10 A, and other parameters are the same as Embodiment 1. FIG. 3A shows microstructure characteristics of the copper-titanium coating, further including elementary copper, copper-nickel intermetallic compound, and a copper-titanium intermediate phase (copper-titanium intermetallic compound) in addition to a nickel-titanium alloy phase from a substrate. Wherein, the relatively obvious copper-nickel intermetallic compound indicates that, during the deposition process of the copper-titanium coating, it is likely to form a transition layer including a copper-nickel intermetallic compound phase between the nickel-titanium substrate and the coating because the temperature on the surface of the substrate is higher, and the atomic radius and electron concentration of copper atoms are very close to that of the nickel atom. This transition layer is advantageous for the improvement of the bonding force between the copper-titanium coating and the nickel-titanium substrate. When the deposition temperature of the coating is too low, it is disadvantageous for the formation of the copper-nickel intermetallic compound and the formation of the transition layer, so that the bonding force of the copper-titanium coating is poor at this time. If it is assumed that the sputtering bias voltage is reduced to 50V, the gas flow is reduced, the pressure of the vacuum chamber is lowered to 0.3 Pa, and other conditions remains unchanged, the XRD graph of the obtained copper-titanium coating is shown in FIG. 3B, where only the elementary copper, the copper-nickel intermetallic compound and the nickel-titanium alloy phase from the substrate are observed. The titanium content of the copper-titanium coating in FIG. 3B is about 25%, but the XRD graph does not show a titanium-containing crystalline phase (in addition to the nickel-titanium alloy substrate) at all. Therefore, the titanium atoms in the copper-titanium coating mainly present in an amorphous state. As both the gas pressure of the vacuum changer and the sputtering bias voltage are reduced during the preparation process of the coating, the density of the charge particles in the vacuum chamber and the energy of the charge particles accelerating to the instrument surface will be reduced if, which are disadvantageous for the formation of the copper-titanium intermetallic compound. Meanwhile, as the temperature of the instrument surface is even lower than the recrystallization temperature (550° C.-650° C.) of titanium atoms and the titanium atoms reaching the instrument surface are bonded to the copper-titanium coating substantially in an amorphous state, the degree of crystallinity of titanium in the coating is reduced so that the XRD diffraction peaks do not show the titanium-containing crystalline phase (in addition to the diffraction peak of the nickel-titanium alloy substrate). A higher sputtering bias voltage may make the temperature on the nickel-titanium alloy surface of the fine component (support rods) rise rapidly, so the deposited copper-titanium coating contains much copper-titanium intermediate phase. When the sputtering bias voltage is lower, the surface temperature of the fine nickel-titanium alloy component rises slowly, so that the deposited copper-titanium coating mainly includes the elementary copper phase, amorphous titanium-containing particles and copper-nickel intermetallic compound.

Figure 4:
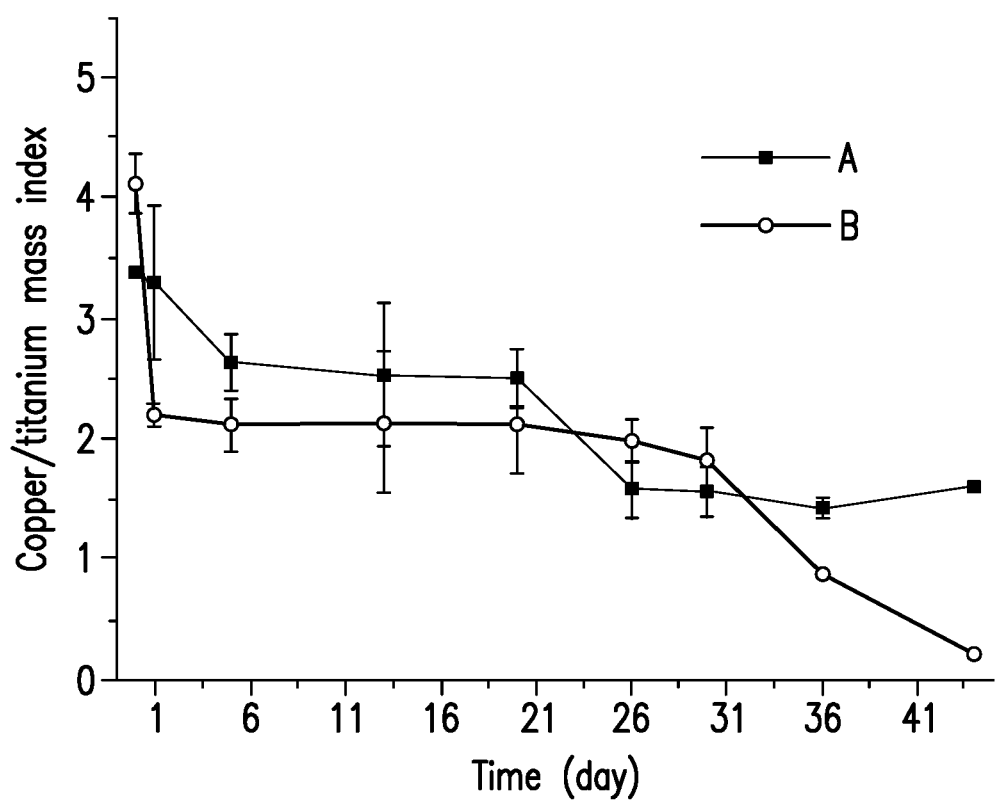
FIG. 4 shows curve graphs of copper/titanium mass indexes changing over time when two different copper-titanium coatings are degraded in in-vitro simulated liquid, where curve A and FIG. 3A are corresponding to a same coating, and curve B and FIG. 3B are corresponding to a same coating.

A filter with the above copper-titanium coating is soaked in human body simulated liquid (phosphate buffer solution PBS), and then copper/titanium content analysis is carried out on the surface of the sampled filter by an X-photoeletron spectroscopy (EDS) after a certain soaking period. As the titanium element in the copper-titanium coating is relatively corrosion-resistant, the titanium content in the copper-titanium coatings of the same batch of samples is basically the same, and remains unchanged. Although the titanium content measured by EDS includes titanium in the nickel-titanium substrate of a filter, the titanium contents of the copper-titanium coatings of the filters of the same batch of samples and the same soaking conditions are normalized, but the copper content belongs to the copper-titanium coatings, so that a ratio (herein referred to as copper/titanium mass index) of the copper content to the titanium content is calculated through the measured copper element and titanium content, and the copper/titanium mass index of a copper-titanium coatings under different corrosion conditions may be obtained. Therefore, the copper/titanium mass index indirectly reflects the mass of copper element resided in the coating. The change in the index may reflect a change rule of the copper content in the copper-titanium coating during corrosion. FIG. 4 shows changes of the copper/titanium mass indexes when the copper-titanium coatings in FIG. 3A and FIG. 3B are degraded in the human body simulated liquid (PBS) over time. It can be seen that, as the corrosion of the copper-titanium coating is conducted, the copper ions in the coatings are released slowly, and the copper/titanium mass indexes are gradually reduced. However, after the coatings are degraded for 1 day, the release rates of the copper ions in the two copper-titanium coatings are different. The copper ions of the copper-titanium coating A at a higher sputtering bias voltage are resealed more slowly, and stably released at a very low release rate after one week; while the copper ions of the copper-titanium coating B at a lower sputtering bias voltage are released rapidly, and the release rate of the copper ions becomes stable after 1 day. Particularly, 5 weeks later, the difference between the copper/titanium mass indexes in the coating A and the coating B is further enlarged. With reference to the structural characteristics shown in FIG. 3A, it is indicated that, when the copper-titanium coating includes much copper-titanium intermediate phase, the readily corrodible elementary copper phase will be completely corroded within several days while the remaining copper-titanium intermediate phase has better corrosion resistance, so that the release rate of the copper ions of the copper-titanium coating is from high to low. As a certain copper ion release rate cannot be kept for a long time, many copper elements remained in the copper-titanium coating cannot be released finally. The copper-titanium coating shown in FIG. 3B contains much elementary copper phase and less copper-nickel intermetallic compound, the titanium element mainly presents in the coating in an amorphous form and the titanium-containing amorphous substance basically does not influence the corrosion of the copper atoms in the coating, so the majority of copper atoms in the copper-titanium coating in FIG. 3B presents in an elementary form. Accordingly, a certain copper ion release rate can still be remained after 30 days, and almost all the copper elements are released after 50 to 60 days, so such a copper-titanium coating is more suitable for clinical application.

The therapeutic functionalities of the medical instrument coating provided by the present mainly lie in that: the coating can continuously release a certain concentration of copper ions for a long term to inhibit the growth of cells on the nickel-titanium alloy surface, but the copper-titanium intermediate phase generated during preparation of the coating is disadvantageous for the long-term continuous release of copper ions, and a lower sputtering bias voltage may inhibit the formation of the copper-titanium intermediate phase. Therefore, the preferable range of the sputtering bias voltage is from 50V to 100V. Similarly, properly reducing the gas flow to reduce gas pressure and reduce the number of charged particles also can avoid the surface temperature of the fine nickel-titanium alloy component (support rods) from increasing rapidly. For example, the copper-titanium coating obtained by changing the argon flow and reducing the pressure of the vacuum chamber to 0.3 Pa basically does not contain any copper-titanium intermediate phase, so the preferable pressure range is from 0.3 Pa to 0.5 Pa.

Copper is one of microelements which human body needs. The normal content of copper in an adult is 100-150 mg, and the normal value of the copper content in blood is 5-8 mg. The copper content of the copper-titanium coating may be controlled, but the copper content in the copper-titanium coating on the surface of the whole recoverable filter is lower than 1.5 mg. It is expected that the copper-titanium coating releases the majority of copper element after 60 days and 0.005 μg/ml of copper ions are released into blood every day, this is far lower than the normal value 1 μg/ml of copper in blood. Therefore, the copper ion release rate in FIG. 4 is basically safe to human body.

Embodiment 3

Common intravascular stents are also made of nickel-titanium alloy, and also have many fine support rods (their cross-sectional area is not more than 3 mm$^2$). With reference to the method described in the forgoing embodiments, preparing a copper-titanium coating on the surface of an intravascular stent may improve the recoverability of the intravascular stent, and does not damage the mechanical property of the intravascular stent.

Figure 5A:
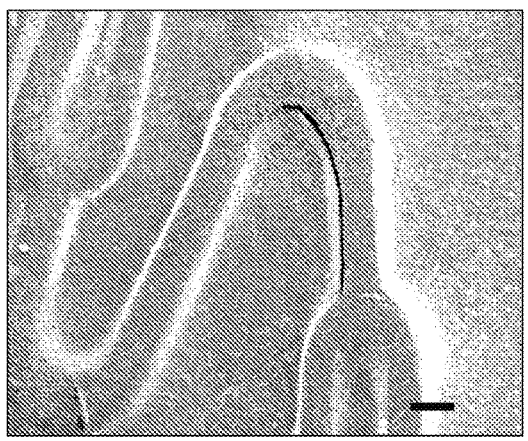
FIG. 5A is a picture when an intravascular stent having a copper-titanium coating containing 20% of copper is implanted in an animal body for one month, where the surface of the stent has been endothelialized.
Figure 5B:
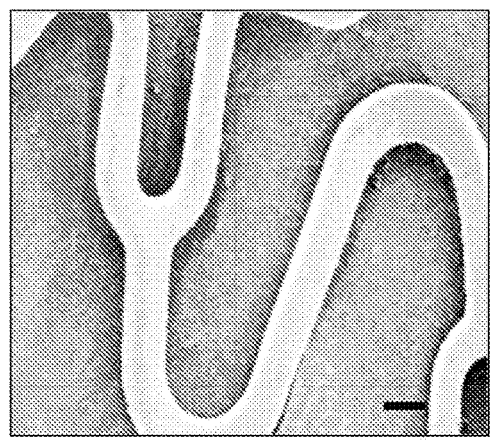
FIG. 5B is a picture when an intravascular stent having a copper-titanium coating containing 40% of copper is implanted in an animal body for one month, where there are basically no cells on the surface of the stent.
Figure 5C:
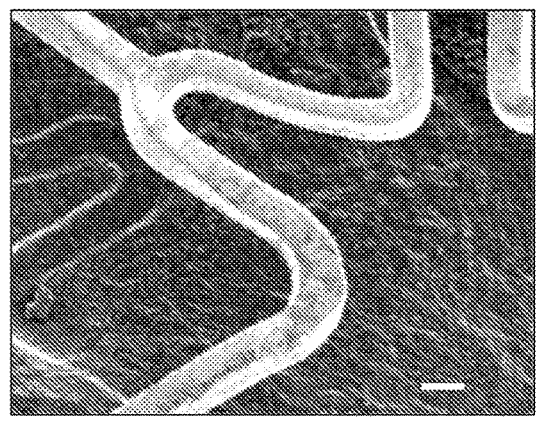
FIG. 5C is a picture when an intravascular stent having a copper-titanium coating containing 60% of copper is implanted in an animal body for one month, where there are basically no cells on the surface of the stent.

FIGS. 5A, 5B and 5C show pictures when an intravascular stent having a copper-titanium coating is implanted in animal body for one month, which may simulate the conditions of the implantation in human body. The copper mass percentage of the copper-titanium coating of the intravascular stent shown in FIG. 5B is 40%, while the copper mass percentage of the copper-titanium coating of the intravascular stent shown in FIG. 5C is 60%. After the intravascular stent is implanted in animal body for one month, the two copper-titanium coatings can completely prevent the encapsulation of cells on the surface of the intravascular stent. In contrast, after the intravascular stent having a copper-titanium coating containing 20% of copper shown in FIG. 5A is implanted in animal body for one month, the surface of the nickel-titanium has been completely endothelialized. Therefore, if the copper-titanium coating is deposited on the surface of a fine nickel-titanium alloy component by plasma sputtering, to ensure the effectiveness of the coating in inhibiting endothelial climbing, the copper content in the copper-titanium coating should be at least more than 20%.

Actually, the corrosion rate of copper in human body monotonically increases with the increasing concentration of γ-globulin or hemoglobin. Just because lots of hemoglobin, albumin and γ-globulin are contained in blood, the copper ion release rate of the copper-titanium coating in a blood environment is higher than that in an in-vitro simulated environment. To ensure the copper-titanium coating to effectively inhibit cell growth, the copper content of the coating on the surface of a medical instrument needs to be higher than that in an in-vitro test environment. Preferably, the copper content of a copper-titanium coating on the surface of a fine nickel-titanium alloy component is higher than 40%.

In combination with the data in FIG. 2 and FIG. 5B, to simultaneously realize good blood compatibility and effective inhibition to the endothelialization of the surface of a medical instrument, particularly for a fine nickel-titanium alloy component of a medical instrument, the copper mass percentage in a copper-titanium coating preferably ranges from 40% to 80%.

In combination with the data in FIG. 1, FIG. 3 and FIG. 4, to ensure the mechanical property of a fine nickel-titanium alloy component and assure a copper-titanium coating to continuously release copper ions, the preferable conditions for the preparation of a copper-titanium coating include: a temperature range from 100° C. to 200° C., a pressure range from 0.3 Pa to 0.5 Pa, a sputtering bias voltage range from 50V to 100V, a sputtering pulse width range from 15 ms to 30 ms, a pulse duty ratio range from 20% to 90%, and a deposition time range from 10 min to 30 min.

The foregoing description merely shows preferred embodiments of the present invention and is not intended to limit the present invention. Any modification, equivalent replacement, improvement and so on made within the spirit and principle of the present invention shall fall into the protection scope of the present invention.

The invention claimed is:

1. A medical instrument coating, being coated on a surface of a nickel-titanium alloy component of a medical instrument, characterized in that the medical instrument coating comprises an elementary copper phase, an amorphous titanium-containing substance, and a transition layer comprising a copper-nickel intermetallic phase, characterized in that the medical instrument coating substantially has no copper-titanium intermediate phase, wherein the majority of copper atoms is in an elementary state.

2. The medical instrument coating according to claim 1, characterized in that a copper content of the medical instrument coating is 40% to 80%.

3. The medical instrument coating according to claim 1, characterized in that the thickness of the medical instrument coating is 200 to 300 nm.

4. The medical instrument coating according to claim 1, characterized in that, in human body, the majority of copper elements of the medical instrument coating can be released in form of copper ions.

5. The medical instrument coating according to claim 1, characterized in that, in human body, the time required for releasing all the copper elements of the medical instrument coating is 50 to 60 days.

* * * * *